US00PP12049P2

(12) United States Plant Patent
Walden

(10) Patent No.: US PP12,049 P2
(45) Date of Patent: Aug. 14, 2001

(54) MINIATURE ROSE PLANT NAMED 'JACRYBI'

(75) Inventor: John K. Walden, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/400,726

(22) Filed: Sep. 21, 1999

(51) Int. Cl.[7] ..... A01H 5/00
(52) U.S. Cl. ..... Plt./123
(58) Field of Search ..... Plt./116, 122, 123, Plt./117

*Primary Examiner*—Howard J. Locker
(74) *Attorney, Agent, or Firm*—Klarquist Sparkman Campbell Leigh & Whinston, LLP

(57) ABSTRACT

A miniature rose plant having red and yellow bicolor flowers; pointed ovoid buds; dark green, glossy foliage; and upright, vigorous, dwarf plant habit.

1 Drawing Sheet

The present invention relates to a new and distinct variety of rose plant of the miniature class which was originated by me by crossing an unnamed seedling with an unnamed seedling.

The primary objective of this breeding was to produce a new miniature (dwarf) rose variety having red and yellow bicolor flowers; pointed ovoid flower buds; dark green, glossy foliage; and a vigorous, upright plant habit. The objective was substantially achieved, along with other desirable improvements, as evidenced by the following unique combination of characteristics that are outstanding in the new variety and that distinguish it from its parents, as well as from all other varieties of which I am aware:

1. Red and yellow bicolor flowers (red, with a yellow petal reverse);
2. Pointed ovoid flower buds;
3. Dark green, glossy foliage;
4. Upright, vigorous, dwarf plant habit.

Asexual reproduction of this new variety by cuttings, as performed as Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (unnamed seedling×unnamed seedling).

*Pollen parent.*—Unnamed seedling (unnamed seedling×unnamed seedling).

Classification:

*Botanical.*—*Rosa hybrida.*

*Commercial.*—Miniature rose.

FLOWER

Observations made from specimens grown in a garden environment at Somis and Wasco, Calif. from May 1995 through August 1999.

Blooming habit: Recurrent.

Bud:

*Size.*—About one inch long when the petals start to unfurl.

*Form.*—The bud form is pointed ovoid; broad based.

*Color.*—When sepals first divide, bud color is near Yellow Group 10C. When half blown, the outer portion of the upper sides of the petals are between Red Group 46A and Red Group 46B, with the bottom ⅓ being Yellow Group 10A; and the lower sides of the petals are Yellow Group 10C with a tinge of Red Group 52D near the petal edge.

*Sepals.*—Color: Predominantly Yellow-Green Group 146B, and Greyed-Red Group 178B. Surface texture: Slightly rough, glandular. There are three normally appendaged sepals. There are two unappendaged sepals with hairy edges.

*Receptacle.*—Color: Near Yellow-Green Group 146D. Shape: Funnel. Size: Broad; small (about 5/16 inch×5/16 inch). Surface: Smooth.

*Peduncle.*—Length: Long (about 1¾ to 2 inches). Surface: Rough; glandular. Color: Greyed-Red Group 178B where exposed to direct sunlight; otherwise Yellow-Green Group 146D. Strength: Stiff; erect.

Bloom:

*Size.*—Medium. Average open size is 2½ inches.

*Borne.*—Singly and several together in pyramidal clusters of three to seven blooms.

*Stems.*—Strength: Strong. Average length is about 8–10 inches.

*Form.*—When first open: High centered. Permanence: All petals curl.

*Petalage.*—Number of petals under normal conditions: 25.

*Color.*—The upper sides of the petals are Red Group 46B. The reverse sides of the petals are Yellow Group 10C. The base of each petal has a large Yellow Group 10A spot approximately 7/16 inch× 7/16 inch. The major color on the upper side is Red Group 46B.

*Variegations.*—The guard petal often has a striation (Yellow Group 10C) running the length of the petal. This same striation is sometimes apparent on the inner petals as well.

*Discoloration.*—The general tonality at the end of the first day: Red Group 46B. At the end of the third day: Red Group 46B. With further aging, color is between Red Group 53A and Red Group 53B.

*Fragrance.*—Slight tea scent.

Petals:

*Texture.*—Thick; leathery.

*Shape.*—Pointed; deltoid.

*Form.*—Edges moderately quilled.

*Arrangement.*—Imbricated (regularly arranged). Petaloids in the center are few; large.

*Persistence.*—Petals drop off cleanly before drying.

*Lastingness.*—On the plant: Long (about seven to eight days). As a cut flower: Not tested.

Reproductive parts:

*Anthers.*—Size: Medium. Quantity: Many. Color: Near Yellow-Orange Group 20A. Arrangement: Regular around styles.

*Filaments.*—Color: Near Yellow-Orange Group 20A.

*Pollen.*—Color: Yellow-Orange Group 20A.

*Styles.*—Color: Near Red Group 47B.

*Stigmas.*—Color: Near White Group 155A.

Plant:

*Form.*—Bush.

*Growth.*—Vigorous; dwarf; upright; branching. At maturity, height is 22–24 inches, width is 18 inches.

Foliage: Number of leaflets on normal mid-stem leaves: Five.

*Size.*—Medium (4 inches long×2⅛ inches wide).

*Quantity.*—Normal.

*Color.*—New foliage: Upper and lower surfaces: Greyed-Purple Group 183A. Old foliage: Upper surface: Near Yellow-Green Group 147A. Lower surface: near Yellow-Green Group 147B.

Leaflets:

*Shape.*—Broadly oval.

*Texture.*—Leathery; glossy.

*Edge.*—Serrated.

*Serration.*—Double.

*Petiole rachis.*—Color: Greyed-Purple Group 183A.

*Petiole underside.*—Smooth; With prickles.

*Stipules.*—Medium (about ¾ inch long), with serrated glandular margins.

*Disease resistance.*—Resistant to rust; susceptible to mildew and blackspot under normal growing conditions.

Wood:

*New wood.*—Color: Near Greyed-Purple Group 183B, rapidly turning green. Bark: Smooth; glabrous.

*Old wood.*—Color: Yellow-Green Group 146B. Bark: Smooth.

Prickles:

*Quantity.*—On main canes from base: Ordinary. On laterals from main canes: Ordinary.

*Form.*—Long (⅜ to 7/16 inch); straight to hooked downward.

*Color when young.*—Greyed-Purple Group 183B.

*Color when mature.*—Near Greyed-Orange Group 165B.

Small prickles:

*Quantity.*—On main stalks: None. On laterals: None.

I claim:

1. A new and distinct variety of rose plant of the miniature class, substantially as herein shown and described, characterized particularly by its red and yellow bicolor flowers; pointed ovoid buds; dark green, glossy foliage; and upright, vigorous, dwarf plant habit.

* * * * *

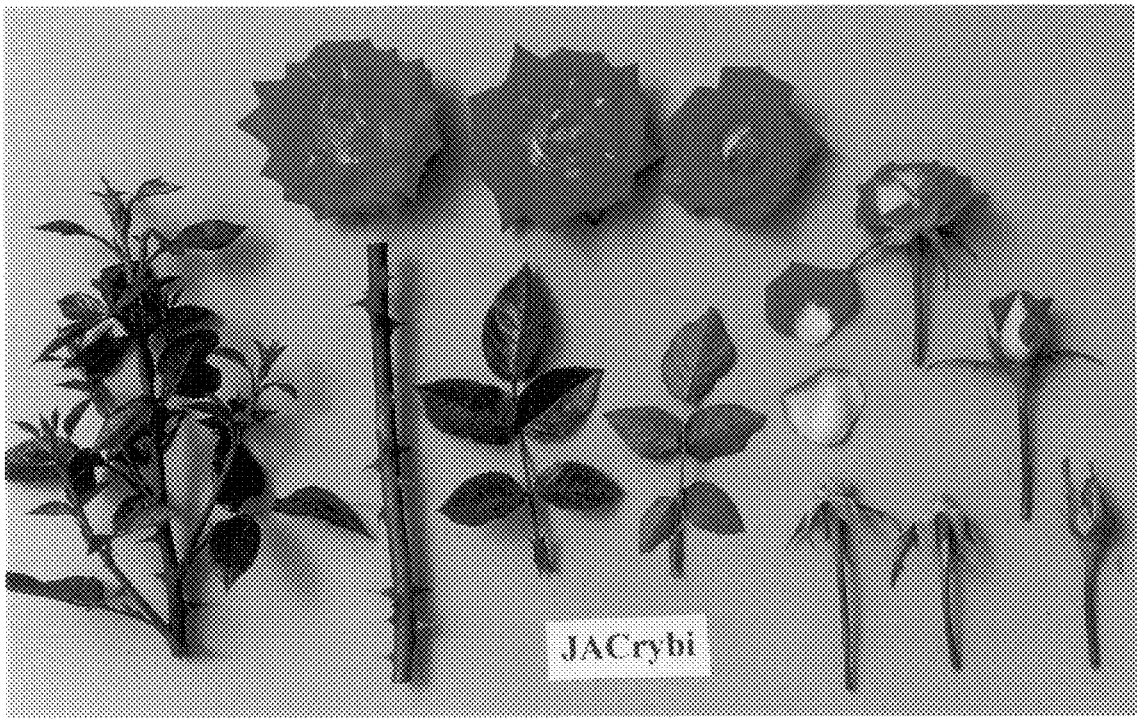
JACrybi